US008134002B2

(12) United States Patent
Huang

(10) Patent No.: US 8,134,002 B2
(45) Date of Patent: Mar. 13, 2012

(54) PROCESS FOR PREPARING OXYMORPHONE

(75) Inventor: Bao-Shan Huang, Plainsboro, NJ (US)

(73) Assignee: Penick Corporation, Pennsville, NJ (US)

( * ) Notice: Subject to any disclaimer, the term of this patent is extended or adjusted under 35 U.S.C. 154(b) by 0 days.

(21) Appl. No.: 12/446,171

(22) PCT Filed: May 2, 2007

(86) PCT No.: PCT/US2007/068009
§ 371 (c)(1),
(2), (4) Date: Aug. 31, 2010

(87) PCT Pub. No.: WO2008/048711
PCT Pub. Date: Apr. 24, 2008

(65) Prior Publication Data
US 2011/0009634 A1  Jan. 13, 2011

Related U.S. Application Data

(60) Provisional application No. 60/829,817, filed on Oct. 17, 2006, provisional application No. 61/007,897, filed on Dec. 14, 2006.

(51) Int. Cl.
C07D 489/08 (2006.01)
C07D 489/02 (2006.01)
(52) U.S. Cl. ........................... 546/45; 546/44
(58) Field of Classification Search .................... 546/45, 546/44
See application file for complete search history.

(56) References Cited

U.S. PATENT DOCUMENTS

| 3,332,950 | A | 7/1967 | Blumberg et al. |
| 3,433,791 | A | 3/1969 | Bentley |
| 3,812,132 | A | 5/1974 | Grew et al. |
| 5,071,985 | A | 12/1991 | Andre et al. |
| 5,869,669 | A | 2/1999 | Huang et al. |
| 5,922,876 | A | 7/1999 | Huang et al. |
| 5,948,788 | A | 9/1999 | Huang et al. |
| 5,952,495 | A | 9/1999 | Huang et al. |
| 6,008,354 | A | 12/1999 | Huang et al. |
| 6,008,355 | A | 12/1999 | Huang et al. |
| 6,013,796 | A | 1/2000 | Huang et al. |
| 6,177,567 | B1 | 1/2001 | Chiu et al. |
| 6,187,782 | B1 | 2/2001 | Nagase et al. |
| 6,262,266 | B1 | 7/2001 | Chiu et al. |
| 6,291,675 | B1 | 9/2001 | Coop et al. |
| 6,365,742 | B1 | 4/2002 | Mudryk et al. |
| 6,395,900 | B1 | 5/2002 | Coop et al. |
| 6,403,798 | B2 | 6/2002 | Chiu et al. |
| 6,723,894 | B2 | 4/2004 | Fist et al. |
| 6,864,370 | B1 | 3/2005 | Lin et al. |
| 7,071,336 | B2 | 7/2006 | Francis et al. |
| 7,129,248 | B2 | 10/2006 | Chapman et al. |
| 7,153,966 | B2 | 12/2006 | Casner et al. |
| 7,851,482 | B2 | 12/2010 | Dung et al. |
| 2002/0045755 | A1 | 4/2002 | Coop et al. |
| 2006/0009479 | A1 | 1/2006 | Bailey et al. |
| 2006/0173029 | A1 | 8/2006 | Chapman et al. |
| 2008/0045716 | A1 | 2/2008 | Smith et al. |
| 2008/0125592 | A1 | 5/2008 | Huang |
| 2008/0146601 | A1 | 6/2008 | Dung et al. |
| 2008/0312442 | A1 | 12/2008 | Buehler et al. |
| 2009/0270624 | A1 | 10/2009 | Weigl et al. |
| 2010/0081820 | A1 | 4/2010 | Jarvi et al. |
| 2010/0274019 | A1 | 10/2010 | Huang |

FOREIGN PATENT DOCUMENTS

| AU | 2007224221 A1 | 9/2007 |
| EP | 0359647 | 3/1990 |
| EP | 0 418 591 | 3/1991 |
| EP | 0 915 094 | 5/1999 |
| WO | 99/02529 | 1/1999 |
| WO | 01/29048 A2 | 4/2001 |
| WO | 2005/028483 | 3/2005 |
| WO | 2007/103105 A2 | 9/2007 |
| WO | 2010/039216 | 4/2010 |

OTHER PUBLICATIONS

Coop et al., "L-Selectride as a General Reagent for the O-Demethylation and N-Decarbomethoxylation of Opium Alkaloids and Derivates" *Journal of Organic Chemistry* vol. 63, No. 13, pp. 4392-4396 (1998).
Weiss, U., "Derivatives of Morphine. II Demethylation of 14-hydroxycodeinone, 14-Hydroxymorphinone and 8,14-Dihydroxydihydromorphinone" *Journal of Organic Chemistry* No. 22, pp. 1505-1508 (1957).
Supplementary European Search Report issued in connection with European Application EP 07 85 4091, dated Oct. 20, 2009.
Supplementary European Search Report issued in connection with European Application EP 07 84 0163, dated Oct. 16, 2009.
U.S. Appl. No. 13/013,569 to Huang, filed Jan. 25, 2011.
European Office Action that issued with respect to patent family member European Patent Application No. 07840163.5 on Mar. 18, 2011.
U.S. Appl. No. 12/446,172 which is the National Stage of PCT/US07/81513 to Bao-Shan Huang, filed Oct. 16, 2007 and entitled "Process for Preparing Oxymorphone, Naltrexone, and Buprenorphine;".
U.S. Appl. No. 11/873,093, filed Oct. 16, 2007 and entitled "Process for Preparing Oxymorphone, Naltrexone, and Buprenorphine."
Extended European Search Report issued with respect to European App. No. 10166419.1, dated Apr. 27, 2011.
Extended European Search Report issued with respect to European App. No. 10166417.5, dated Apr. 21, 2011.
Marton et al., "Herstellung von 6,14-Ethenomorphinan-Derivaten" *Liebigs Ann. Chem.*, pp. 915-919, 1993.
Klein et al., "Electrophilic α-Methylene-γ-lactone and Isothiocyanate Opioid Ligands Related to Etorphine" *J. Med. Chem.*, vol. 33, pp. 2286-2296, 1990.

(Continued)

Primary Examiner — Charanjit Aulakh
(74) Attorney, Agent, or Firm — Greenblum & Bernstein, P.L.C.

(57) ABSTRACT

Methods are provided which include converting oripavine to other opiates, including converting oripavine to 14-hydroxymorphinone and/or converting 14-hydroxymorphinone to oxymorphone. Purification and salt formation are optionally included.

11 Claims, No Drawings

OTHER PUBLICATIONS

Schwartz et al., "Efficient Synthesis of 14-Hydroxymorphinans from Codeine" *J. Med. Chem.*, vol. 24, No. 12, pp. 1525-1528, 1981.

Andre et al., "O-Demethylation of Opioid Derivatives with Methane Sulfonic Acid / Methionine: Application to the Synthesis of Naloxone and Analogues" *Synthetic Communications*, vol. 22, No. 16, pp. 2313-2327, 1992.

Hosztafi, "Reactions of Azodicarboxylic Esters with Amines" *Scientia Pharmaceutica*, vol. 55, pp. 61-75, 1987.

Marton et al., "Herstellung von 6,14-Ethenomorphinan-Derivaten" *Monatshefte für Chemie*, vol. 125, pp. 1229-1239, 1994.

European Office Action issued in connection with European Application EP 07 84 0163.5, dated Dec. 21, 2009.

Australian Examination Report dated Aug. 22, 2011 for patent family member Australian Patent Application No. 2007311152.

Australian Examination Report dated Aug. 22, 2011 for patent family member Australian Patent Application No. 2007313103.

PROCESS FOR PREPARING OXYMORPHONE

CROSS-REFERENCE TO RELATED APPLICATIONS

This application claims priority to U.S. Provisional Application Ser. No. 60/829,817, filed Oct. 17, 2006, and U.S. patent application Ser. No. 11/611,049, filed Dec. 14, 2006, for which a Request to Convert Non-Provisional Application to Provisional Application Under 37 C.F.R. §1.53(c)(2) has been granted and assigned U.S. Provisional Application Ser. No. 61/007,897, the contents of which are incorporated by reference in their entirety.

BACKGROUND OF THE INVENTION

1. Field of the Invention

This invention relates to preparation of opiates such as 14-hydroxymorphinone, oxymorphone and naloxone from oripavine.

2. Background of the Invention and Related Art

Oxymorphone, a potent opiate analgesic, is a semi-synthetic substitute for morphine. It is about ten times as potent as morphine. In the United States, FDA has approved oxymorphone hydrochloride in oral, parenteral and suppository form. Naltrexone, methylnaltrexone, buprenorphine, nalmefene, nalorphine and naloxone are other useful opiates.

Oxymorphone can also be converted to these and other useful compounds, such as nal-compounds, including naloxone.

Oxymorphone is typically synthesized using thebaine, morphine or another compound as a starting material. Thebaine, when used, is generally obtained from the concentrated poppy straw (CSP-T), a poppy extract relatively rich in thebaine. Reaction schemes for producing oxymorphone from thebaine take several steps, to intermediates such as oxycodone, then conversion of the 3-methoxy group of oxycodone to the 3-hydroxy group of oxymorphone. U.S. Pat. No. 6,291,675, for example, discloses a method for O-demethylation of the 3-methoxy group of opiates by use of a lithium hydride compound, providing a yield of O-demethylated opioid of at least 23%. U.S. Pat. No. 5,922,876 discloses preparation of oxymorphone from morphine. The process includes protection of the 3-hydroxy group of morphine with an aceto or benzyl group.

Syntheses according to the present invention do not include the conversion of a 3-methoxy group present on opiates to a 3-hydroxy group, and are therefore expected to result in increased reaction efficiencies, such as reduced reaction complexities and increased yield.

DETAILED DESCRIPTION OF THE PREFERRED EMBODIMENTS

It has been found that oripavine can be economically converted to other opiates, such as oxymorphone and derivatives thereof. Any starting material comprising oripavine may be used. The starting material preferably comprises greater than about 50% by weight oripavine, preferably greater than about 70%, more preferably greater than about 95%. The starting material is preferably purified oripavine, or a concentrate of poppy straw comprising oripavine as the main alkaloid (CPS-O).

Preferably, the oripavine comprises "natural oripavine," but can also comprise any source of oripavine. By "natural oripavine" is meant oripavine obtained directly from a natural source (e.g., botanical, bioengineered bacterial, etc.), and is meant to distinguish from oripavine obtained in a laboratory or factory setting by partial or total chemical synthesis, e.g., synthetic or semi-synthetic oripavine. Natural oripavine includes, without limitation, CPS-O, and purified oripavine obtained from CSP-O or other poppy straw.

Preferably, oripavine is oxidized with an oxidizing agent to obtain 14-hydroxymorphinone. The 14-hydroxymorphinone is then preferably reduced with a reducing agent to obtain oxymorphone. The 14-hydroxymorphinone can also be used in other ways, preferably to prepare other products.

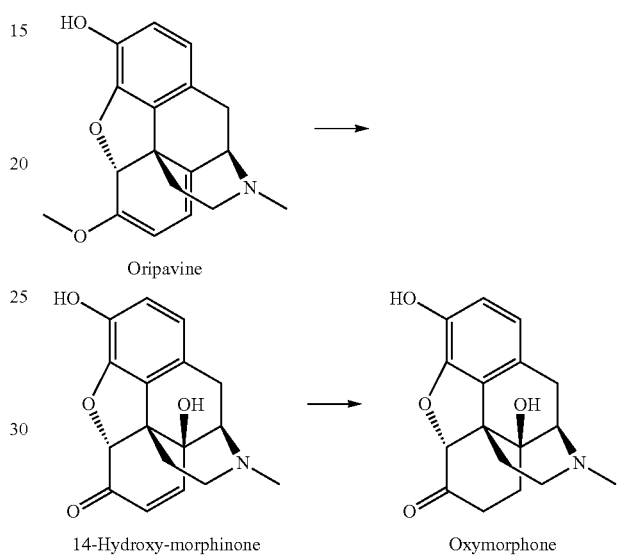

The oxidizing agent can comprise any oxidizing agent that permits the conversion of oripavine to 14-hydroxymorphinone, including, but not limited to, peroxy acids, such as performic acid, peracetic acid, and m-chloroperoxybenzoic acid (MCPBA). Mixtures of oxidizing agents may be used. When a peroxy acid is used, it may be added, or prepared in situ.

When the oxidizing agent comprises a peroxy acid prepared in situ, it may be prepared in any manner, preferably by combining a peroxide and an acid. Any peroxide or combination of peroxides that can provide a peroxy acid can be used, preferably hydrogen peroxide, for example, aqueous hydrogen peroxide. Any acid or combination of acids that can provide a peroxy acid can be used, preferably formic acid, or acetic acid, for example, aqueous solutions of formic and/or acetic acid. Performic acid may be obtained, for example, by combining hydrogen peroxide and formic acid, and peracetic acid may be obtained by combining hydrogen peroxide with acetic acid.

The reaction may be carried out in any appropriate solvent, preferably an aqueous solvent. When the oxidizing agent includes a peroxy acid, it is preferred to use a solvent comprising the corresponding acid. For example, when the oxidizing agent comprises performic acid, it is preferred to use a solvent comprising formic acid, and when the oxidizing agent comprises peracetic acid, it is preferred to use a solvent comprising acetic acid. When MCPBA is used, it is preferred to use a solvent comprising acetic acid.

An exemplary process using performic acid as oxidizing agent is:

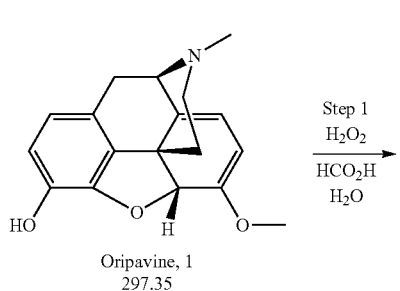

Oripavine, 1
297.35

Step 1
H₂O₂
HCO₂H
H₂O

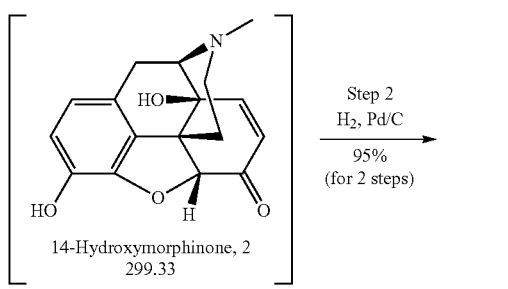

14-Hydroxymorphinone, 2
299.33

Step 2
H₂, Pd/C
95%
(for 2 steps)

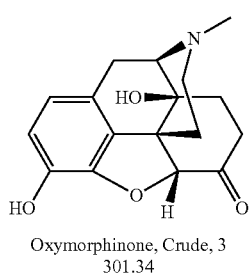

Oxymorphinone, Crude, 3
301.34

An exemplary process using MCPBA as oxidizing agent is:

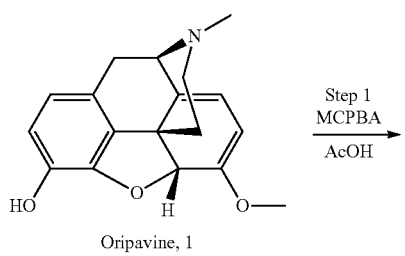

Oripavine, 1
297.35

Step 1
MCPBA
AcOH

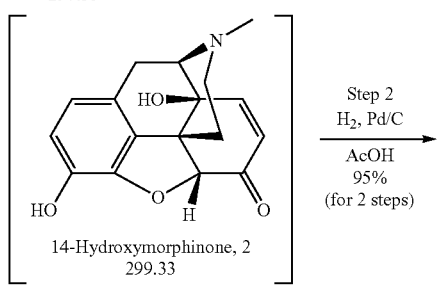

14-Hydroxymorphinone, 2
299.33

Step 2
H₂, Pd/C
AcOH
95%
(for 2 steps)

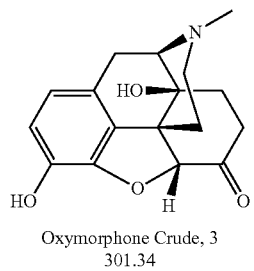

Oxymorphone Crude, 3
301.34

Any temperature that permits the reaction to proceed may be used. The temperature need not remain constant, and may vary during the reaction. Higher reaction temperatures speed up the reaction, but may increase formation of by-products. Different oxidation agents may run optimally at different temperatures. Reactions employing performic acid, for example are preferably run in the range of about 20 to 60° C., more preferably about 40-50° C., even more preferably at about 50° C. Reactions employing MCPBA are preferably run in the range of about 0 to 40° C., more preferably about 10-30° C., even more preferably at about ambient temperature, e.g., about 25° C.

The reaction is run under conditions to convert oripavine to 14-hydroxymorphinone. Preferably, at least about 90% of the oripavine is converted to 14-hydroxymorphinone, more preferably, about 95%, even more preferably about 98% or 99%. Preferably, the conversion of oripavine to 14-hydroxymorphinone will be about 100%.

The remaining amount of oripavine in the reaction mixture, as well as the amount of 14-hydroxymorphinone produced can be determined by any method, preferably by TLC or HPLC.

Any reducing agent may be used to convert 14-hydroxymorphinone to oxymorphone. Catalytic hydrogenation is a preferred method, e.g., with palladium catalyst, preferably Pd/C.

Catalytic hydrogenation may be performed at any suitable pressure, and is preferably done completely, or in part, in a low pressure environment. Catalytic hydrogenation preferably includes hydrogenation at or greater than, about 1 atmosphere pressure. By "low pressure" is preferably meant less than about 10 atm, or less than about 4 atm. Catalytic hydrogenation reactions, therefore, include hydrogenation at, e.g., at about 1-10 or about 1-4 atm. Low pressure hydrogenation generally requires less expensive processing and/or lower equipment costs than hydrogenation at higher pressures.

The oxidizing and reduction may be performed as a "one pot" process, or may be done in separate vessels. The 14-hydroxymorphinone may be isolated, but need not be isolated, prior to reduction. In a preferred embodiment, the 14-hydroxymorphinone is not isolated in solid form prior to reduction.

Preferably, the opiate, e.g., oxymorphone, or a salt thereof, is purified. Preferably, crude oxymorphone is isolated, purified, and converted to a salt, preferably the hydrochloride salt. An exemplary process for purifying crude oripavine base is:

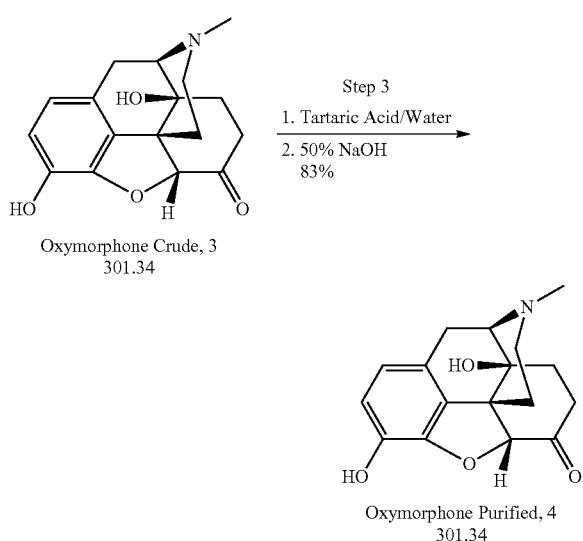

Step 3
1. Tartaric Acid/Water
2. 50% NaOH
83%

Oxymorphone Crude, 3
301.34

Oxymorphone Purified, 4
301.34

Purification aids may be used in the purification process. Preferred purification aids include adsorbents. Some preferred purification aids include activated carbon (commercially available as, e.g., Darco), and/or powdered cellulose (commercially available as, e.g., Solka-Floc). The reducing agent sodium bisulfite may be used, e.g., when performing the reaction in the presence of oxidants, e.g., under an oxidizing atmosphere. When the reaction is run under a non-oxidizing atmosphere, e.g., nitrogen gas, it may be possible to omit sodium bisulfite. Other purification aids, including purification aids known in the art, may be selected and used by a person of ordinary skill in the art.

Opiate salts, e.g., of oxymorphone may also be prepared. Any salt, preferably a therapeutically acceptable salt, is included in the present invention. The hydrochloride is a preferred salt. Methods for preparing salts of compounds are known in the art. An exemplary process for preparing the hydrochloride salt of purified oxymorphone is:

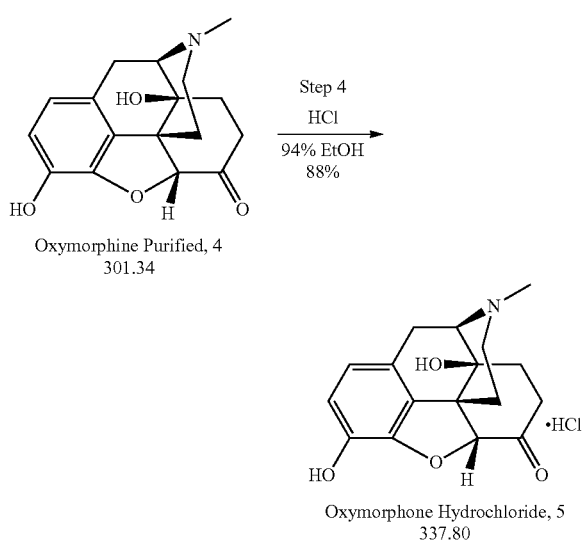

Step 4
HCl
94% EtOH
88%

Oxymorphine Purified, 4
301.34

Oxymorphone Hydrochloride, 5
337.80

Generally, oxymorphone, preferably purified oxymorphone, is suspended or dissolved in a liquid, preferably an alcohol and/or water; and more preferably ethanol, 2-propanol, combinations thereof, and combinations with water. Then, an acid, such as hydrochloric acid (preferably concentrated or gaseous HCl), is added to the mixture. After cooling for a period of time, preferably once the reaction is complete or substantially complete, the oxymorphone salt is separated from the mixture, washed, and dried.

Oxymorphone, or salt thereof, preferably oxymorphone HCl, may be prepared into pharmaceutical dosage forms. Pharmaceutical dosage forms include, but are not limited to, tablets, pills, capsules (including hard or soft gelatin capsules), parenteral formulations, suppositories, patches and powders. Generally, a salt, e.g., the hydrochloride, is preferred. Oxymorphone base may be used, e.g., for transdermal patches. Preferred dosage forms include parenteral formulations and suppositories.

Oxymorphone can also be converted to other compounds, such as naloxone. Methods for effecting this conversion are known in the art.

EXAMPLES

Example 1

Crude Oxymorphone from Oripavine

To a stirred oripavine (166.7 mg; 0.561 mmol) solution in 0.5 mL 30% formic acid (4.185 mmol) is added 0.1 ml 30% hydrogen peroxide (0.979 mmol), and the resulting mixture is stirred at 50° C. After complete transformation as indicated by TLC, the reaction mixture is transferred to a Parr Shaker, and 5% Pd/C (51.9 mg) is added. The mixture is hydrogenated at room temperature under 28 inch-Hg overnight, filtered, basified with $NH_4OH$, and extracted with methylene chloride (5×15 ml). The extract is evaporated under reduced pressure to give 113.4 mg of a pale yellow solid, yield 67.1%. The product has an identical retention time in HPLC and same $R_f$ value in TLC to an oxymorphone standard.

Example 2

Crude Oxymorphone from Oripavine

Oripavine (50.0 g, 168 mmol), de-ionized water (70 ml) and 90% formic acid (42.0 g, 0.821 mol) are charged into a 500 ml 3-necked round bottom flask. The solution is stirred at 30-40° C. and to the composition is added 35% hydrogen peroxide drop-wise (19.7 g, 0.203 mol) while keeping the temperature below 40° C. Upon completion of the addition, the mixture is stirred at 40-50° C. for 4 hours. The reaction mixture is transferred to a 1-L hydrogenation vessel and 5% Pd/C (3.2 g) and 2-propanol (160 ml) are added. Hydrogenation proceeds at 46-52 psig at room temperature overnight (about 18 h). The catalyst in the mixture is filtered off. The filtrate and washings are combined and basified with 50% NaOH (59.6 g) to pH 9.16. The temperature is kept at below 30° C. during the basification. The slurry is stirred at room temperature for 1 hour, and filtered to give a brown solid, which is then dried at 90° C. and 25" Hg vacuum overnight to provide the crude oxymorphone as light brown solids (48.2 g, 160 mmol, 95.2% yield).

Example 2b

Crude Oxymorphone from Oripavine

Oripavine (50.0 g, 168 mmol), is converted to 14-hydroxymorphinone as in Example 2 through and including addition of hydrogen peroxide. Upon completion of the addition, the mixture is stirred at 40-50° C. By HPLC, it is determined that the area ratio of 14-hydroxymorphinone:oripavine is 27.2:72.8 after 1 hour, and 99.3:0.7 after 4 hours. After 4 hours 40 minutes, the reaction mixture is transferred to a 1-L hydrogenation vessel and 5% Pd/C (3.2 g) (Degussa E101 o/w, $H_2O$ 56.2%) is added. Hydrogenation proceeds at 46-52 psig at room temperature overnight (about 18 h). The mixture is filtered, and rinsed with about 50 ml water. 250 ml of filtrate are obtained, to which is added 25 ml butanol, yielding a mixture having pH of 2.86. While kept at less than 30° C., or at about 19.6° C., the filtrate is basified with 57.5 g of 50% NaOH, resulting in a pH of 9.05. The mixture is stirred for about one hour at room temperature, filtered, washed with water (4×50 ml), yielding a brown solid. The wet cake is dried at 93° C. at 25" Hg overnight, yielding 44.2 g, 87.2% yield, of oxymorphone as a light brown solid.

Example 3

Crude Oxymorphone from CPS-O

A mixture of CPS-0 (6.92 g contains 76% (5.26 g, 17.7 m mol) of oripavine), meta-chloroperoxybenzoic acid (MCPBA, 4.30 g) and glacial acetic acid (52 ml) is stirred at room temperature for 5 hours. The amount of oripavine is then expected to be not more than 1% by HPLC analysis. To the resulting 14-hydroxymorphinone mixture is added 5% Pd/C (0.55 g) and hydrogenation proceeds at room temperature at 48 psig of hydrogen for about 18 hours. The amount of unreacted 14-hydroxymorphinone is expected to be not more than 0.5% by HPLC analysis. The mixture is filtered to remove the catalyst and the filtrate is evaporated to almost dryness. The residue is dissolved in water and basified to pH 9 by ammonium hydroxide. The solids are collected by filtration and dried at 90° C. and under 25-inch Hg of vacuum for 3 hours to give crude oxymorphone (approximately 95% yield expected).

Example 4

Purified Oxymorphone

A suspension of the crude oxymorphone (20.0 g, 66 mmol) and water (120 ml) is stirred at 45-55° C. Tartaric acid (5.5 g) is added to adjust the pH to 4.35 to complete dissolution. Darco (1.0 g) and Solka-floc (1.0 g) are added and stirred at 45-55° C. for 1 hour. The mixture is filtered and rinsed with water (10 ml). The filtrate and washings are combined and to this are added Darco (1.0 g), Solka-floc (1.0 g) and sodium bisulfite (0.4 g). The mixture is stirred for 1 hour at 45-55° C., filtered and rinsed with water (10 ml). 1-BuOH (12 ml) is added to the filtrate and stirred at 45-55° C. 50% NaOH (6.1 g) is added to adjust the pH to 8.56 at 45-55° C., in particular, 50.5° C. The slurry is cooled to room temperature and filtered. Light brown solids are collected and dried at 65° C. and 25" Hg vacuum overnight to give purified oxymorphone (18.2 g, 60 m mol, 91.0% yield).

Example 5

Oxymorphone HCl from Purified Oxymorphone

Purified oxymorphone (17.8 g, 59 mmol) is suspended in 94% aq. ethanol (107 ml) and stirred at 50-60° C. Concentrated hydrochloric acid (32%) is added slowly to adjust the pH to 2.58. The mixture is allowed to cool to room temperature, and then cooled further to 0-10° C., stirred for 2 hours and filtered then washed with ethanol (3×20 ml). The isolated solids are dried at 75° C. under 25 inches-Hg overnight to give oxymorphone HCl as white solids (17.3 g, 51 mmol, 86.7% yield).

This Oxymorphone HCl meets the specifications in the USP 2006 monograph for Oxymorphone Hydrochloride.

Although the invention has been described with reference to particular means, materials, and embodiments, it should be noted that the invention is not limited to the particulars disclosed, and extends to all equivalents within the scope of the claims.

What is claimed is:

1. A method of preparing oxymorphone or a salt thereof comprising:
    oxidizing oripavine to obtain 14-hydroxymorphinone, wherein said oxidizing is performed in a single step with an oxidizing agent comprising performic acid, peracetic acid or m-chloroperoxybenzoic acid in a solvent comprising formic acid or acetic acid; and
    reducing the 14-hydroxymorphinone to obtain oxymorphone.
2. The method of claim 1 wherein the solvent comprises formic acid when the agent comprises performic acid.
3. The method of claim 1 wherein the solvent comprises acetic acid when the agent comprises peracetic acid or m-chloroperoxybenzoic acid.
4. The method of claim 1 wherein the reducing includes catalytic hydrogenation.
5. The method of claim 1 wherein the reducing comprises palladium-catalyzed hydrogenation.
6. The method of claim 4 wherein the hydrogenation includes hydrogenation at low pressure.
7. The method of claim 1 further comprising converting the oxymorphone to an oxymorphone salt.
8. The method of claim 7 wherein the oxymorphone salt comprises oxymorphone hydrochloride.
9. The method of claim 1 further comprising purifying the oxymorphone or salt thereof.
10. The method of claim 9 comprising recrystallizing the oxymorphone or salt thereof.
11. The method of claim 1 wherein the oripavine includes oripavine present in a concentrate of poppy straw comprising oripavine as the main alkaloid.

* * * * *